United States Patent [19]

Wu

[11] Patent Number: 5,891,454
[45] Date of Patent: Apr. 6, 1999

[54] ANTI-CANCER DRUG AND SPECIAL TUMOR NECROTIZING AGENT

[75] Inventor: John Y. J. Wu, San Francisco, Calif.

[73] Assignees: Alexander Wu; John Wu; Jenny Gwo Wu; Lester Wu, all of San Francisco, Calif.

[21] Appl. No.: 827,274

[22] Filed: Mar. 28, 1997

[51] Int. Cl.$^6$ .................................................. A61F 2/00
[52] U.S. Cl. ...................... 424/423; 514/946; 514/947; 514/604
[58] Field of Search ........................... 514/604, 946, 514/947; 424/423

[56] References Cited

U.S. PATENT DOCUMENTS 4,241,084  12/1980  Minuto .................................. 424/313
5,414,014  5/1995  Schneider et al. ..................... 514/535
5,552,153  9/1996  Behl ...................................... 424/449

Primary Examiner—Thurman K. Page
Assistant Examiner—Lakshmi Channavajjala
Attorney, Agent, or Firm—Chi Ping Chang

[57] ABSTRACT

This invention provides a novel pharmaceutical composition exhibiting remarkable anti-cancer, and cancer necrotizing properties as well as other desirable pharmacological properties. The composition is a mixture of toluene sulfonamide (e.g. para toluene sulfonamide) with a specifically designed solution which consists of polyethylene glycol, 2-ethyl-1,3-hexanediol, propanediol, decanedioic acid, dimethyl, sulfoxide and ethanol. The composition demonstrates promising therapeutical activity in preliminary human clinical tests and exhibits very little undesirable side effects.

41 Claims, No Drawings

ANTI-CANCER DRUG AND SPECIAL TUMOR NECROTIZING AGENT

FIELD OF INVENTION

This invention relates to pharmacology and medicine. In particular, it relates to a novel pharmaceutical composition exhibiting remarkable anti-cancer and cancer necrotizing activities as well as exhibiting astonishing cancer related pain killing properties. More specifically, the present invention provides for a new series of anti-cancer drags and cancer narcotizing agents which produce significantly less side effects (such as hair loss, suppression of WBC and bone marrow) in cancer therapy than those of the conventional chemotherapy.

BACKGROUND OF INVENTION

Toluene sulfonamide is widely known as a highly effective anti-fungal agent exhibiting anti-fungal activity against fungal infected plant tissues and human skin. For instance, Harry Pugh disclosed in 1967 that para-toluene is highly effective as a topical agent for the treatment of skin fungal diseases. According to Pugh, such anti-fungal activity is achieved by incorporating para-toluene sulfonamide with propylene glycol to form a 7–8% solution by weight. However, toluene sulfonamide has never been reported as an anticancer agent, nor has it been reported as an cancer necrotizing agent.

It is theoretically possible that a compound exhibiting anti-fungal activity may also possess other biocidal activities either by the same anti-fungal mechanism or by an entirely different mechanism. In the field of cancer therapy, it is likely that a compound inhibiting fungal growth in plant cells may inhibit the growth of cancer cells found in human tissue. As such, the inventor conceives and believes that toluene sulfonamide might be effective in killing human cancer cells in light of its effectiveness in killing fungi found in plant cells.

Many existing cancer drugs are hampered by unwarranted side effects which may severely limit their applications. It is therefore desirable to have an anti-cancer drug which exhibits a potent anti-cancer activity without producing any significant adverse side effects to a human recipient. Furthermore, a desirable anti-cancer drug shall be compatible with or be complementary with other anti-cancer drugs or cancer therapy to provide a synergistic effect when used in conjunction with such others.

It is generally agreed that the activity of a drug may vary significantly with the ways such drug is prepared or formulated. This is particular true for many anticancer drugs which are not readily dissolvable in an aqueous solution or in water based solvents and, consequently, render the preparation of a therapeutically active concentration impractical. In order to achieve a maximum therapeutical benefit for a given drug, the drug should be properly formulated in accordance with its physical and chemical properties to form a desirable solution or mixture so that a therapeutically active concentration is readily achievable.

It is therefore an object of the present invention to provide for a novel composition comprising para-toluene sulfonamide exhibiting a remarkable anti-cancer and cancer necrotizing properties with significantly less harmful side effects than those of conventional chemotherapy treatments.

It is another object of the invention to provide for a novel formulation comprising para-toluene sulfonamide prepared in a solution or mixture which facilitates dissolution of para-toluene sulfonamide in the solution by a percentage weight basis to provide a therapeutically active concentration for cancer therapy.

It is a further object of the invention to provide for a method of providing therapeutical benefits for a human patient in cancer therapy employing a novel composition comprising para-toluene sulfonamide.

SUMMARY OF THE INVENTION

This invention relates to a novel pharmaceutical composition exhibiting remarkable anti-cancer and cancer necrotizing activities with significantly less side effects such as hair loss, suppression of WBC and bone marrow in cancer therapy than those of the conventional chemotherapy.

One aspect of the invention is to provide for a pharmaceutical composition exhibiting anti-cancer and tumor necrotizing activity in both in vitro and in vivo evaluation as well as in human investigation. The pharmaceutical composition comprises at least one toluene sulfonamide in an amount of 10–80 percent by weight of said composition, a solution prepared from a group of chemicals, consisting essentially of polyethylene glycol, 2-ethyl-1.3-hexanediol, propanediol, decanedioic acid, dimethyl sulfoxide, and ethanol in which the solution may be in an amount of 90–20 percent by weight of the composition, and the toluene sulfonamide is added to the solution on a percentage weight basis to from a mixture sufficient to exhibit said anti-cancer and tumor necrotizing activity. A preferred pharmaceutical composition according to the invention comprises toluene sulfonamide in an amount of 30% by weight of said composition.

Another aspect of the invention is to provide for a method of preparing a pharmaceutical composition exhibiting both in vitro and in vivo as well as in human patient anti-cancer and tumor necrotizing activity. The method comprises weighing at least one toluene sulfonamide in an amount of 10–80 percent by weight of the composition, preparing a solution from a group of chemicals consisting essentially of polyethylene glycol, 2-ethyl-1.3-hexanediol, propanediol, decanedioic acid, dimethyl sulfoxide, and ethanol wherein the solution may be in an amount of 90–20 percent by weight of the composition followed by adding the toluene sulfonamide to the solution on a percentage weight basis to from a mixture sufficient to exhibit said anti-cancer and tumor necrotizing activity.

One more aspect of the invention is to provide for a method for providing therapeutical benefits to a human patient diagnosed with a cancer lesion. The method comprises preparing a pharmaceutical composition exhibiting anti-cancer and tumor necrotizing activity described above followed by injecting the human patient repeatedly with an amount of said pharmaceutical composition each with an adequate interval sufficient to exhibit its anti-cancer and tumor necrotizing activity in the human patient. A preferred way for injection involves injecting the pharmaceutical composition directly to a cancer lesion or a tumor cell.

One further aspect of the invention is to provide for a method for necrotizing a cancer or a tumor cell in a human patient to provide therapeutical benefits to the patient. Briefly, the method comprises injection of the cancer or tumor cell repeatedly, each with an adequate interval, with an amount of the pharmaceutical composition sufficient to exhibit tumor necrotizing activity in the human patient.

According to the invention, the toluene sulfonamide of the pharmaceutical composition may comprise a group of toluene sulfonamide analogs consisting of para-toluene sulfonamide, orthotoluene sulfonamide, N-ethyl orthotoluene, N-ethyl para-toluene sulfonamide, N-cyclohexyl para-toluene sulfonamide or mixtures thereof.

DETAILED DESCRIPTION OF INVENTION

EXAMPLE I

The Pharmaceutical Composition and Preparation of A Preferred Anti-Cancer and Cancer Necrotizing Agent According to the invention A preferred embodiment of an anti-cancer and cancer necrotizing agent according to this invention comprise a mixture of a group of chemical ingredients consisting essentially of para-toluene sulfonamide, polyethylene glycol, 2-ethyl-1,3-hexanediol, propanediol, decanedioc acid, dimethyl sulphoxide and ethanol. Among these chemicals, paratoluene is the major compound that exhibits anti-cancer and cancer necrotizing activities. However, since para-toluene sulfonamide is not readily dissolved in water or in a water-based solution, it is critical to develop a suitable formulation which will facilitate the mixing or dissolution of paratoluene sulfonamide in or with a group of solvents or surfactants. The desirable solvents, used alone or in combination with para-toluene sulfonamide, should not exhibit any harmful or adverse effects to a human receipient as will be illustrated later by the invention.

1. Preparation of the Anti-Cancer and Cancer Necrotizing Agent

All the chemical ingredients employed to form the anti-cancer and cancer necrotizing agent described above according to the invention are commercially available chemicals without resorting to cumbersome techniques or specialized equipment. The process of preparation of this novel composition is as follows:

A. Preparation of A Main Ingredient

1. Para-toluene sulfonamide is the main ingrident of the anti-cancer and cancer necrotizing agent of the invention. An adequate amount of para-toluene sulfonamide sufficient to provide a desirable therapeutic activity is weighed in a white crystal form for the preparation of the anti-cancer drug. However, it should be noted that the main ingredient is not limited to para-toluene sulfonamide. Instead, it may include a series of toluene sulfonamide analogs including, but not limited to, orthotoluene sulfonamide, N-ethyl orthotoluene, N-ethyl para-toluene sulfonamide, N-cyclohexyl para-toluene sulfonamide or mixtures thereof The amount of this main ingredient may vary from 10% to 80% by weight of the solution or mixture to which the main ingrident is dissolved.

B. Preparation of A Specifically Designed Solution:

A specifically designed solution consists essentially of polyethylene glycol, 2-ethyl-1, 3-hexanediol, propancdiol, decanedioic acid, dimethyl sulphoxide and ethanol is prepared by mixing together an adequate amount of each of the chemicals on a percentage weight basis as is set forth in Table 1. The specifically designed solution is used as a solvent for preparation of the anti-cancer drug provided by the invention.

C. Preparation of the Novel Composition:

The main ingredient, para-toluene sulfonamide, is then added to the specifically designed solution. The mixture will soon become cloudy and turbid followed by proper stirring and heating (i.e., 80° C.–105° C.) of the mixture until a clear yellowish oily liquid is obtained. This oily liquid is the novel anti-cancer and cancer nacrotizing drug according to the invention (hereinafter may be referred to as "Immunsyn E").

D. The Bottling:

The The above oily liquid mixture is heated to 60° C. and is then filtered through a 0.22 micromembrane filter and fill antispeptically. The resulting filtrate is filled into 5 ml and 3 ml ampules or vials and sterilized at 105° C. for 45 minutes. Test sterilit.

TABLE 1

A Preferred Weight Percentage of the Ingredients of Immunsyn E

| Chemicals | Source | % Weight |
|---|---|---|
| (a) The main ingredient | | |
| Para-toluene sulfonamide | (*1) | 30% |
| (b) The specifically designed solution | | |
| Polyethylene Glycol | (*2) | 35.5% |
| 2-ethyl-1,3-hexandiol | (*3) | 16.4% |
| Propanediol | (*4) | 8.2% |
| Decanedioic acid | (*5) | 3.7% |
| Dimethyl sulphoxide | (*6) | 6.7% |
| Ethanol | (*7) | 1.5% |

(*1) Akzo Chemicals Co., and The Monsanto Co, USA
(*2) Guangzhou Chemical Reagent Factory, China
(*3) Dixie Chemical Co., USA
(*4) Rohm & Hass Co., USA, and Guangzhou Chemical Reagent Factory, China
(*5) Guangzhou Chemical Reagent Factory, China
(*6) Guangzhou Chemical Reagent Factory, China
(*7) Guangzhou Chemical Reagent Factory, China It should be noted that the pharmaceutical composition of the preferred anti-cancer and cancer necrotizing agent provided by the invention as set forth in Table 1 (i.e., Immunsyn E) is by no means the only composition which exhibits such activity. In fact, as shown in Table 2, the pharmaceutical composition of the anti-cancer and cancer necrotizing agent according to the invention may be varied by varying the respective percentages of each of the constituting ingredients without significant deviations from its characteristic anti-cancer and cancer necrotizing activity (i.e., "Immunsyn C").

TABLE 2

The Variation in Weight Percentages of the Constituting Ingredients of the Anti-Cancer and Cancer Nacrotizing Agent Acccording to the Invention

| Chemicals | Source | % Weight |
|---|---|---|
| (a) The main ingredient | | |
| Para-toluene sulfonamide | (*1) | 10%–80% |
| (b) The specifically designed solution | | |
| Polyethylene Glycol | (*2) | 10%–60% |
| 2-ethyl-1,3-hexandiol | (*3) | 5%–30% |
| Propanediol | (*4) | 2%–30% |
| Decanedioic acid | (*5) | 1%–15% |
| Dimethyl sulphoxide | (*6) | 0%–20% |
| Ethanol | (*7) | 0%–20% |

(*1) Akzo Chemicals Co., and The Monsanto Co, USA
(*2) Guangzhou Chemical Reagent Factory, China
(*3) Dixie Chemical Co., USA
(*4) Rohm & Hass Co., USA, and Guangzhou Chemical Reagent Factory, China
(*5) Guangzhou Chemical Reagent Factory, China
(*6) Guangzhou Chemical Reagent Factory, China
(*7) Guangzhou Chemical Reagent Factory, China The anti-cancer and cancer necrotizing activity of the Immunsyn E according to the invention has been proven and determined by a series of in vitro and in vivo biochemical and pharmarcological tests as well as by human clinical investigation.

EXAMPLE II

Inhibitory Effects of Immunsyn E on the Growth of Three Tumor Cell Lines In Vitro.

The inhibitory effects of the Immunsyn E against the growth of three tumor cell lines in vitro are investigated by Guangzhou Institute for Chemical Carcinogenesis, Guangzhou, China in accordance with the method published in Guangzhou Lung Cancer Journal, Dec. 20, 1996, pg. 80, which is incorporated herein by reference. The three tumor cell lines, A-549 (human lung cancer), H7402 (hepatic cancer line), CNE (nasopharyngeal cerelnoma) and a human fibroblast cell line (HFF), which is used as a control cell line, are evaluated for the in vitro inhibition tests. These cell lines were cultured in a medium containing 10% bovine serum albumin prior to harvest. Before commencement of the in vitro evaluation, these cell lines were suspended in vials at a concentration of 1.5×105 cells per 5 ml medium. The cells were cultured in the presence of $CO_2$ for 24 hours followed by incubating these cells with a series of Immunsyn E (345 mg/ml) at 0.01, 0.02, 0.04, 0.08 and 0.1 ul/ml medium. A control blank received no Inuunsyn E. The experiments were evaluated at 24, 48 and 72 hours post incubation. Triplicate samples from each concentration were determined for cell survival rate and percentage growth inhibition.

The results, as shown in Table 3 and Table 4 below, demonstrate that Immunsyn E inhibits the growth of three tumor cells. The effect of inhibition was correlated with the doses of Immunsyn E. The inhibitory effect in human normal cells (i.e., human fibroblast) was less than those in the three tumor cells. In view of $IC_{50}$, the nasopharyngeal carcinoma, CNE, and the lung cancer cells, A-549, seem to be more sensitive in Immunsyn E growth inhibition tests than the hepatic cancer cells, H7402.

EXAMPLE III
Anti-Turnor Effects of Immunsyn E. on Mouse Transplanted Liver Tumor and Sarcoma S. 180

The anti-tumor effects of the Inmunsyn E are evaluated in vivo on mouse transplanted liver tumor and Sarcoma S. 180 by researchers from the Institute of Cancer Research, University of Sun Yat-sen for Medical Sciences, Guangzhou, China. A solvent blank (i.e., the specifically designed solution illustrated in Table 1), a saline blank as a positive control are used as controls for the in vivo tests. As per the Drug Administration Law of the People's Republic of China, and the rules governing observation of the pharmacodynamic study of the therapy action, the tumors were surgically removed from tumor infected mice and were homogenized to form suspensions followed by filtration to make a suspension solution at $1×10^6$–$10^7$ cell/ml. The suspension was injected (i.e., 0.2 ml per mice) into the test mice for tumor growth until the transplanted tumor cells were established and grew up to a size of 0.5×0.5 cm. The inhibition of mouse transplanted liver tumor and Sarcoma S.180 are evaluated by a series of doses of Inmunsyn E as illustrated in Tables 5 and 6 below for 10 days. The Immunsyn E was administered to mice through muscle injection. For each mouse, a 0.2 ml aliquot of Immunsyn E was administered. At the end of the in vivo tests, several parameters such as mouse body weight, average tumor weight and percentage of tumor inhibition, are determined. The growth inhibition rates of the transplanted tumors by Immunsyn E were determined in accordance with the following formula:

TABLE 3

Inhibitory Rate (%) of Different Cells Following Immunsyn E. Exposure

| Concentration (ul/ml) | A-549 (exposure time/hour) 24 h, 48 h, 72 h | | | H 7402 (exposure time/hour) 24 h, 48 h, 72 h | | | CNE (exposure time/hour) 24 h, 48 h, 72 h | | | HFF (exposure time/hour) 24 h, 48 h, 72 h | | |
|---|---|---|---|---|---|---|---|---|---|---|---|---|
| 0.00000 | | | | | | | | | | 100 | 100 | 100 |
| 0.00345 | 23 | 37 | 42 | 22 | 28 | 26 | 17 | 26 | 59 | | | |
| 0.00690 | 38 | 58 | 67 | 30 | 39 | 29 | 49 | 63 | 27 | 17 | 35 | 38 |
| 0.01380 | 42 | 66 | 62 | 62 | 57 | 54 | 72 | 81 | 20 | 45 | 42 | 54 |
| 0.02760 | 60 | 76 | 73 | 75 | 89 | 63 | 84 | 80 | 28 | 57 | 65 | 72 |
| 0.03450 | 72 | 85 | 85 | 70 | 87 | 78 | 92 | 88 | 22 | | | |

A-549: human lung cancer
H7402: hepatic cancer
CNE: nasopharyngeal cerelnoma
HFF: human fibroblasth

TABLE 4

Median Inhibitory Concentration ($IC_{50}$) for the Different Cells of Table 3 Following Immunsyn E Exposure

| | $IC_{50}$ (mg/ml) | | | |
|---|---|---|---|---|
| | Cell Type | | | |
| Time | A-549 | H7402 | CNE | HFF |
| 24 h | 0.0169 | 0.0117 | 0.0112 | 0.0202 |
| 48 h | 0.0058 | 0.0086 | 0.0055 | 0.0173 |
| 72 h | 0.0043 | 0.0127 | 0.0029 | 0.0101 |

A-549: human lung cancer
H7402: hepatic cancer
CNE: nasopharyngeal carcinoma
HFF: human fibroblast % inhibition rate=(average tumor weight of the solvent group or (N.S.)–average tumor weight of the Immunsyn E treated group)/ average tumor rate of the solvent group The results, as shown in tables 5 and 6, demonstrate that Immunsyn E is effective to inhibit the growth of mouse transplanted liver tumor and sarcoma S-180 in varying degrees at the doses of 172.5, 345.0 and 690.0 mg/kg/day for 10 days (i.e., 1.0 ml contains 345 mg of Immunsyn E). The solvent used in this experiment has no anti-tumor effects toward mouse liver tumor and sarcoma S-180 at dose 2 ml/kg/day×10 d (i.e., for 10 days). The results clearly indicate that Immunsyn E possesses a significant anti-tumor effect toward mouse liver and sarcoma S-180 at the doses chosen in this experiment.

TABLE 5

The Effect of Immunsyn E on the Growth of Mouse Liver Tumor (I.M.)***

| Group | Dosage mg/kg/dx10 d | No. Of animals outset | No. Of animals final | Body weight outset | Body weight final | Ave. weight of tumor (x + SD) (g) | Anti-tumor inhibit rate rate % | P Value |
|---|---|---|---|---|---|---|---|---|
| NS(control) + | 2.0 ml/kg | 11 | 11 | 21.5 | 27.8 | 3.05 ± 0.93 | — | |
| Solvent(control) | 2.0 ml/kg | 11 | 11 | 21.9 | 26.0 | 2.56 ± 0.70 | 16.1 | >0.05 |
| CTX | 18.0 | 11 | 11 | 19.9 | 27.9 | 1.81 ± 0.22 | 40.7 | <0.01* |
| "Immunsyn E" | 172.5 | 10 | 9 | 22.1 | 28.1 | 1.76 ± 0.34 | 31.3 | <0.01** |
| | 345.0 | 10 | 9 | 21.9 | 27.8 | 1.48 ± 0.33 | 42.2 | <0.01** |
| | 690.0 | 11 | 9 | 22.2 | 24.1 | 1.24 ± 0.53 | 51.6 | <0.01** |
| NS(control) | 2.0 ml/kg | 11 | 11 | 20.3 | 32.6 | 2.92 ± 0.85 | — | |
| Solvent(control) | 2.0 ml/kg | 10 | 10 | 20.2 | 29.5 | 3.12 ± 0.77 | −6.8 | >0.05 |
| CTX | 18.0 | 11 | 11 | 20.3 | 27.8 | 1.57 ± 0.63 | 46.2 | <0.01* |
| "Immunsyn E" | 172.5 | 11 | 11 | 20.4 | 26.8 | 2.15 ± 0.78 | 31.1 | <0.01** |
| | 345.0 | 10 | 10 | 20.1 | 28.7 | 2.00 ± 0.86 | 35.9 | <0.01** |
| | 690.0 | 11 | 11 | 20.0 | 27.8 | 1.56 ± 0.61 | 50.0 | <0.01** |
| NS(control) | 2.0 ml/kg | 11 | 10 | 20.9 | 28.5 | 2.35 ± 0.61 | — | |
| Solvent(control) | 2.0 ml/kg | 11 | 11 | 20.6 | 28.3 | 2.48 ± 0.64 | −5.5 | >0.05 |
| CTX | 18.0 | 11 | 10 | 20.9 | 28.5 | 0.94 ± 0.41 | 60.0 | <0.01* |
| Immunsyn E" | 172.5 | 11 | 10 | 20.8 | 27.5 | 1.62 ± 0.34 | 34.7 | <0.01** |
| | 345.0 | 12 | 12 | 20.1 | 25.6 | 1.39 ± 0.31 | 43.9 | <0.01** |
| | 690.0 | 14 | 14 | 20.6 | 24.5 | 1.03 ± 0.29 | 58.6 | <0.01** |

*Compared to the saline control group
**Compared to the solvent control group
***I.M. indicates muscle injection
+NS means injectio Natrii Chloride

TABLE 6

The effect of Immunsyn E on the growth of mouse S-180 sarcoma (I.M.)

| Group | Dosage mg/kg/dx 10d | No. Of animals Outset | No. Of animals Final | Body weight Outset Final | Ave. weight of tumor (x ± SD) (g) | Anti-tumor inhibit rate % | P Value |
|---|---|---|---|---|---|---|---|
| NS(control) | 2.0 ml/kg | 11 | 11 | 22.5 30.3 | 2.83 ± 0.97 | — | |
| Solvent(control) | 2.0 ml/kg | 11 | 11 | 22.4 27.1 | 3.03 ± 0.69 | −7.1 | >0.05 |
| CTX | 18.0 | 11 | 11 | 22.4 30.9 | 1.37 ± 0.47 | 51.6 | <0.01* |
| "Immunsyn E" | 172.5 | 11 | 10 | 22.0 29.1 | 1.64 ± 0.68 | 45.9 | <0.01** |
| | 345.0 | 11 | 10 | 22.4 27.5 | 1.76 ± 0.44 | 41.9 | <0.01** |
| | 690.0 | 11 | 9 | 22.4 27.3 | 1.04 ± 0.62 | 65.7 | <0.01** |
| NS(control) | 2.0 ml/kg | 11 | 11 | 22.2 31.0 | 2.76 ± 0.73 | — | |
| Solvent(control) | 2.0 ml/kg | 10 | 10 | 22.3 27.9 | 3.05 ± 0.90 | −10.5 | >0.05 |
| CTX | 18.0 | 10 | 10 | 22.6 29.1 | 1.29 ± 0.43 | 53.3 | <0.01* |
| "Immunsyn E" | 172.5 | 12 | 11 | 22.4 27.4 | 1.79 ± 0.45 | 41.3 | <0.01** |
| | 345.0 | 12 | 11 | 22.6 26.6 | 1.63 ± 0.42 | 44.6 | <0.01** |
| | 690.0 | 12 | 11 | 22.7 27.7 | 1.10 ± 0.30 | 63.9 | <0.01** |
| NS(control) | 2.0 ml/kg | 11 | 11 | 19.1 27.8 | 2.40 ± 0.73 | — | |
| Solvent(control) | 2.0 ml/lkg | 12 | 11 | 19.4 26.2 | 2.33 ± 0.40 | 2.9 | >0.05 |
| CTX | 18.0 | 11 | 10 | 19.3 26.4 | 1.14 ± 0.28 | 52.5 | <0.01* |
| "Immunsyn E" | 172.5 | 11 | 9 | 19.0 25.3 | 1.63 ± 0.39 | 30.0 | <0.01** |
| | 345.0 | 12 | 11 | 19.1 24.5 | 1.37 ± 0.30 | 41.2 | <0.01** |
| | 690.0 | 13 | 11 | 19.5 24.3 | 1.14 ± 0.28 | 50.9 | <0.01** |

*Compared to saline control group
**Compared to solvent control group

EXAMPLE IV

The Therapeutical Effect of Immunsyn E on DMBA Induced Rat Breast Cancer.

The therapeutical effect of Immunsyn E on DMBA induced rat breast cancer was evaluated by Guangzhou Institute for Chemical Carcinogenesis, Guangzhou, China. A group of female rats at age of two months were selected for 7,12-Dimethyl Benz [a] anthracene (DMBA) breast tumor induction. The breast cancer was found in 73% of rats within 6 months by incubating female rats with 20 mg of 7,12-Dimethyl Benz [a] anthracene (DMBA). Once the tumor was formed, 0.38 mg/kg of Inmuunsyn E was injected daily (i.e., 0.2 ml per rat per injection) directly to the inside of the tumor in accordance with a dose conversion of human daily administration (6210 mg/65 kg. body weight/d) for 10 days. The second and third courses were implemented after an interval of 3 days. After 3 courses the size of the DMBA induced rat breast cancer tumor was significantly reduced compared to the control group such that hnmunsyn E exhibited a 90% tumor inhibition rate after first course of treatment, a 84% tumor inhibition rate after second course of treatment and a 96% tumor inhibition rate after the third course of Immunsyn E treatment. The pathological examination also confirmed changes of tumor tissues in the test animals.

EXAMPLE V

The Acute Toxicity Tests of Immunsym E in Mouse

The acute toxicity tests of Immunsyn E are studied in mouse by Institute of Cancer Research, University of Sun Yat-sen for Medical Sciences, Guangzhou, China (May 1996). The Immunsyn administered to mouse through intramuscular injection. Five doses are used to construct a dose-response relationship. The results, as shown in Table 7, indicate that the $LD_{50}$ is 1034.91 mg/kg for mice with the 95% confidence interval between 945–1131.20 mg/kg. The control group, 10 animals were given single intramuscular injection of solvent, records no animal deaths following a 14 day observation. The results suggest that Immunsyn E is fairly safe and has a very low acute toxicity.

TABLE 7

The Result of Acute Toxicity Test of Immunsyn E in Mice (I.M.)

| Group | Dosage (mg/kg) | Logarithmic | No. of Animals | No. of Animal Deaths | Mortality rate in % | Y Value (probability Unit) |
|---|---|---|---|---|---|---|
| 1 | 1207.50 | 3.0818 | 10 | 8 | 80 | 5.8416 |
| 2 | 1086.75 | 3.0361 | 10 | 5 | 50 | 5.0000 |
| 3 | 979.80 | 2.9911 | 10 | 4 | 40 | 4.7567 |
| 4 | 879.75 | 2.9444 | 10 | 3 | 30 | 4.4756 |
| 5 | 790.05 | 2.8979 | 10 | 1 | 10 | 3.7184 |

EXAMPLE VI

The Acute Toxicity Tests of Immunsyn E in Rat

The acute toxicity tests of Inmunsyn E are also evaluated in rat by Institute of Cancer Research, University of Sun Yat-sen for Medical Sciences, Guangzhou, China. The Immunsyn E is administered to rat through intramuscular injection. Five doses are used to construct a dose-response relationship. The results, as shown in Table 8, indicate that the $LD_{50}$ is 1124.52 mg/kg with a 95% confidence interval of 951.30–1177.17 mg/kg for rat. The control group, 10 animals were given single intramuscular injection of solvent, records no animal deaths following a 14 day observation.

TABLE 8

The Result of Acute Toxicity Test of Immunsyn E in Rat (I.M.)

| Group | Dosage (mg/kg) | Logarithmic | No. of Animals | No. of Animal Deaths | Mortality rate in % | Y Value (probability Unit) |
|---|---|---|---|---|---|---|
| 1 | 1725.00 | 3.2368 | 10 | 10 | 100 | 9.8200 |
| 2 | 1380.00 | 3.1399 | 10 | 8 | 80 | 8.7271 |
| 3 | 1140.00 | 3.056 | 10 | 6 | 60 | 5.5271 |
| 4 | 883.20 | 2.9460 | 10 | 3 | 30 | 2.1891 |
| 5 | 707.25 | 2.8496 | 10 | 0 | 0 | 0.4188 |

EXAMPLE VII

The Acute Toxicity Tests of Immunsyn E in SD Rat

The acute toxicity tests of Immunsyn E are also evaluated in SD Rat by Guangzhou Institute for Chemical Carcinogenesis, Guangzhou, China. The hmunsyn E is administered to rat through PR OS (Latin term for "by mouth"). Six doses are used to construct a dose-response relationship. The results, as shown in Table 9, indicate that the $LD_{50}$ is 3959.25 mg/kg with a 95% confidence interval of 3499.37–4479.62 mg/kg for SD rat. The control group, 10 animals were given single intramuscular injection of solvent, records no animal deaths following a 14 day observation. The results suggest again that Immunsyn E is fairly safe and has a very low acute toxicity.

TABLE 9

The Result of Acute Toxicity Test of Immunsyn E in SD Rat (P.O.)

| Group | Dosage (mg/kg) | Logarithmic | No. of Animals | No. of Animal Deaths | Mortality rate in % | Y Value (probability Unit) |
|---|---|---|---|---|---|---|
| 1 | 7210.50 | 3.8579 | 10 | 10 | 100 | 9.7462 |
| 2 | 5768.40 | 3.7611 | 10 | 8 | 80 | 8.8997 |

TABLE 9-continued

The Result of Acute Toxicity Test of Immunsyn E in SD Rat (P.O.)

| Group | Dosage (mg/kg) | Logarithmic | No. of Animals | No. of Animal Deaths | Mortality rate in % | Y Value (probability Unit) |
|---|---|---|---|---|---|---|
| 3 | 4616.10 | 3.6643 | 10 | 7 | 70 | 6.9118 |
| 4 | 3691.50 | 3.5672 | 10 | 3 | 50 | 4.0984 |
| 5 | 2953.20 | 3.4703 | 10 | 2 | 20 | 1.6977 |
| 6 | 2363.23 | 3.3735 | 10 | 0 | 0 | 0.4622 |

$LD_{50}$ = 3959.25 mg/kg  95% confidence interval  3499.37–4479.62 mg/kg

EXAMPLE VIII

Pharmacological Studies of Immunsyn E.

(a) The general pharmacological studies of Immunsyn E.

The general pharmacological studies of Immunsyn E are conducted by the Department of Pharmacology, University of Sun Yat-sen Medical Sciences, China The dogs were given Immunsyn E at doses of 69, 138, 207 mg/kg body weight (equal to 1-fold, 2-fold, and 3-fold of maximum clinical administration) by intramuscular injection. No significant changes in blood pressure, heartbeat rate, electrocardiogram and breath were observed.

(b) The effect of Immunsyn E on central nerve system

The effect of Immunsyn E on mouse free activity was determined. Mice received Immunsyn E at a dose of 276 mg/kg, 552 mg/kg and 690 mg/kg by intraperitoneal and intramuscular injections. The effect of Immunsyn E on mouse free activity was observed. The mouse free activity was reduced after 5 minutes of intraperitoneal injection or 10 minutes of intramuscular injection. The reduction of free activity was correlated with the dose of Immunsyn E. The result indicated that Immunsyn E possesses inhibition effect on central nerve system.

(c) The effect of Immunsyn E on hypogenesis induced by Pentobarbital, Pontobarbital coordinated test and re-fall asleep test were performed. The results demonstrated that Immunsyn E has obvious effects on the central sedation and hypogenesis in mice. Such effect was correlated with the dose of Inmunsyn E.

EXAMPLE IX

Clinical Evaluation of Immunsyn E in Human Patients.

These biomedical research studies involving human participants conform to generally accepted scientific principles and are based upon adequately performed laboratory, animal and human studies previously generated. Most participants were late stage terminally ill cancer patients who were treated with every possible conventional treatment without any improvement. The Immunsyn E treatments were recommended by their respective Oncologists and supervised by the same.

A. Treatment of Sixteen Cases of Terminal Liver Cancer With Immunsyn E:

Sixteen patients each with terminally diagnosed liver cancer were treated with hmmunsyn E. The 16 patients (11 males and 5 females) have an average age of 58 years (i.e., ranging from 39–82 years). Among these 16 patients, 9 patients with original liver cancers, 3 patients whose liver cancers originated from intestinal origins, 4 patients whose liver cancers were originated from stomach, breast, nose and abdomen metatasized to liver. These liver cancers of these patients were diagnosed by ultrasonic scanning and confirmed by CT and other clinical methods as shown in Table 10.

TABLE 10

Clinical Baseline Information for Liver Patients and Number of Treatment with Immunsyn E

| No. | Sex | Age | Diagnosis | Tumor size (mm) | Number of treatment | Total amount (ml) |
|---|---|---|---|---|---|---|
| 1 | F | 51 | originated from abdoma | 45 × 50 | 3 | 9 |
| 2 | M | 38 | originated from intestine | 95 × 110 | 3 | 9 |
| 3 | M | 70 | originated from intestine | 140 × 135 | 14 | 42 |
| 4 | F | 76 | originated from intestine | 45 × 49 | 9 | 27 |
| 5 | M | 58 | originated from liver | 125 × 77 | 5 | 15 |
| 6 | M | 61 | originated from liver | 65 × 43 | 5 | 15 |
| 7 | M | 73 | originated from stomach | 70 × 42 | 9 | 27 |
| 8 | F | 55 | originated from nose | 50 × 34 | 7 | 21 |
| 9 | F | 58 | originated from breast | 40 × 35 | 16 | 48 |
| 10 | F | 57 | originated from liver | 71 × 108 | 2 | 6 |
| 11 | M | 59 | originated from liver | 94 × 96 | 6 | 18 |
| 12 | M | 82 | originated from liver | 117 × 102 | 3 | 9 |
| 13 | M | 54 | originated from liver | 91 × 90 | 8 | 24 |
| 14 | M | 69 | originated from liver | 109 × 104 | 43 | 129 |
| 15 | M | 48 | originated from liver | 91 × 56 | 6 | 18 |
| 16 | M | 49 | originated from liver | 94 × 60 | 6 | 18 |

Each of the patients was injected with 3 ml of Immunsyn E (i.e., equivalent to 1035 mg of immunsyn E) each time, 1–2 times per week. The injection was performed with the aid of ultrasonic scanning probe and injector. The ultrasonic scanning probe provides accurate location of the tumor lesions of each patient. With such aids, Immunsyn E was accurately injected and delivered to the tumor lesions directly. The progress of patients was monitored by ultrasonic scanning of tumor lesions, variation in clinical symptoms, side effects, routine laboratory analysis of kidney and liver functions, blood biochemistry analysis, AFP (i.e., blood test index for general liver cancer) and CT (i.e., a computerized sectional X-ray equipment). The therapeutical effects were determined based on the size of tumors prior to and post the immunsyn E treatment as follows: Complete Remission (CR) indicating total disappearance or liquidation of the tumor; Partial Remission (PR) indicating, more than 50% reduction of the tumor size; MR indicating reduction of tumor size between 25–50%; Stable (SD) indicating less than 25% reduction of tumor size; and Progressive Development (PD) indicating increase of tumor size by at least 25%. All the above therapeutical effects should maintain for at least one month.

The results from routine laboratory analysis of kidney and liver functions, blood biochemistry analysis, AFP and CT indicate that 3 patients have three fold increases of AFP, two patients have two fold decreases in AFP, and one patient restores its AFP to normal. For liver function (eight patients have liver dysfunction prior to Immunsyn treatment), six patients reported significant improvements, two patients restored totally their liver function. For reliving of liver pails (six patients suffered from severe liver pains prior to treatment), two patients reported dramatic reduction of pain, and four patients reported total relief of liver pain. There were no observable side effects other than drowsiness and reduced of appetite which were disappeared 24 hour post treatment.

The reduction of tumor size and changes in ultrasonic image were summarized in Table 11 below for nine patients who have received consecutive Immunsyn E treatment for at least three months. It is clear that changes in tumor lesion ultrasonic image are among the earlier response to Immunsyn E injection. Echo enhancement was reported for all of the patients (9 out of 9) after 1–3 injections of Immunsyn E. Six patients have localized solidification of tumor lesions due to increasing resistance observed for penetration of the injector as well as the delivery of Immunsyn E by injection. Two patients showed localized liquidation of tumor lesions. One of the liquidized tumor lesion was sampled by the injector as a white liquid and subsequent biochemical and pathological analysis of which indicated lack of cancerous cells and red cells in such liquidized area. Five patients showed reduction of tumors. For patient No. 6 of Table 11, its AFP was significantly decreased despite no significant reduction of tumor size. In summary, the short term therapeutic effects indicate 1 CR, 3 PR, 3 MR, 2 SD. The overall therapeutic effect is 44.4% (i.e., CR+PR). The positive treatment effect is 77.8% (i.e., CR+PR+MR).

TABLE 11

Clinical Results Based on Change in Tumor Size and Ultrasonic Image in Patients Nos. 1–9 of Table 10 After Treatment with Immunsyn E

|     |     | Tumor Size | | Echo Enhancement | |
|-----|-----|------------|--|------------------|--|
| No. | Diagnosis | before (mm) | after (mm) | (Ultrason Scan) after treatment | Remarks |
| 1 | originated from abdoma | 45 × 50 | 0 × 0* | + | CR |
| 2 | originated from intestine | 95 × 110 | 95 × 110 | + | SD |
| 3 | originated from intestine | 140 × 135 | 140 × 144** | + | MR |
| 4 | originated from intestine | 45 × 49 | 33 × 24 | + | PR |
| 5 | originated from liver | 60 × 45 | 50 × 30 | + | MR |
| 6 | originated from liver | 65 × 56 | 65 × 50 | + | MR |
| 7 | originated from stomach | 70 × 42 | 62 × 39 | + | SD |
| 8 | originated from nose | 400 × 200 | 23 × 12 | + | PR |
| 9 | originated from breast | 40 × 35 | 29 × 21 | + | PR |

*Localized liquidation of tumor lesions at a size of 50 × 40
**Localized liquidation of tumor size at 90 × 64.

B. Treatment of Recurrent Breast Cancer (1.5 cm×1.5 cm) by Immunsyn E:

A patient with a recurrent breast cancer is treated with Immunsyn E by tumoral injection of Immunsyn E at the dose of 1.5 ml per injection, twice per days and for 7 days. Biopsy of the breast cancer is subsequently performed by doctors in the Canton Province People's Hospital to evaluate the effect of Immunsyn E. The biopsy results indicated that (a) cancer cells in connective tissue found to be all necrotized and partially dissolved; and (b) sweat glands were intact, did not show any unbroken cancer cells.

C. Treatment of Thirteen Cases of Malignant Tumors with Immunsyn E:

Immunsyn E is used to treat thirteen cases of different malignant tumors for tumor regression and reduction through local tumoral injections which are conducted by Guangzhou Municipal Tumor Hospital, Guangzhou, China. Approximately 3 ml–4 ml of Immunsyn E was injected to 4–6 sites of a tumor lesion, one injection per day. The next injection is rotated clockwise around the tumor lesion (so that the same area is not injected). One treatment period requires 3–4 weeks. At the conclusion of the treatment period, the recipient was evaluated for tumor size and disappearance. As shown in Table 12, there are five Complete Remission (CR), three Partial Remission (PR), 2 No Progress (NP), and three Stable (S). The results showed that Immunsyn E can produce significant: tumor regression, size reduction and even total disappearance of tumors.

TABLE 12

Summary of Treatment of Thirteen Cases of Malignant Tumors with Immunsyn E

| Diagnosis | Cases | CR | PR | NP | S | P |
|-----------|-------|----|----|----|---|---|
| Breast Cancer | 2 | 2 | | | | |
| Facial sarcoma | 3 | 1 | 1 | 1 | | |
| Epidermal squamous sarcoma | 2 | | | 2 | | |

TABLE 12-continued

Summary of Treatment of Thirteen Cases of Malignant Tumors with Immunsyn E

| Diagnosis | Cases | CR | PR | NP | S | P |
|---|---|---|---|---|---|---|
| Lung cancer after surgery matasis to intestinal wall | 1 | | | 1 | | |
| Nasopharyngeal ca. after radiation therapy matasis to back of the neck | 1 | 1 | | | | |
| Neck lymphosarcoma | 1 | 1 | | | | |
| Primary liver cancer | 3 | | | | 3 | |
| Total | 13 | 5 | 3 | 2 | 3 | 0 |

Note: (CR) — Complete Remission, (PR) — Partial Remission, (NP) — No Progress, (S) — Stable, (P) — Progress The above 13 recipients (9 males, 4 females, ages 11 to 68 years old) were all late stage cancer patients classified by "TNM" in accordance with A.J.C.C. and U.I.C.C. Most of them had palpable tumors due to recurrency and metastasis. Tumoral injection or muscle injections (I.M.) were applied to most of the patients, a few were treated by intravenous injection ("I.V.) (6 ml of Immunsyn E per person, per day) for 20–30 day treatment periods. All tumor lesions had biopsy reports.

From this very preliminary investigation, we feel that tumoral injection incorporated with I.V. or I.M. of Immunsyn E may be a good way to reduce the tumor size or to eradicate the tumor.

D. Treatment of Lung Cancer Through Local Injection of Immunsyn E via Bronchoscopy Seven patients, 3 with adenocarcinoma at staging IIIa and 4 with squarnous at staging IIIb, were enrolled in the study. All showed lobular atelectasis with complete or incomplete obstruction of the bronchi. Immunsyn E was injected to two to three sites of the tumor lesion with 2–3 ml of Immunsyn E, twice a week for total number of injection of 11–16 times (25–35 ml). The results showed that after the injection, tumor tissue turned white in color, which was easy to remove. The removed tissue was shown microscopically to be necrosis. After one course of injection, partial relief (PR) was shown in all patients. Atelectasis completely disappeared in 3 cases. There was no apparent hemorrhage in the injection sites in all patients, the nearby normal tissue did not show any histological change bronchoscopically and microscopically. The results indicated the local injection of Innunsyn E is an effective and safe management in relieving malignant tumor obstruction of lung cancer.

E. Investigation of Eleven Cases of the Human Cancer Treatment by Immunsyn E by Guangzhou Institute of Respiratory Diseases, Guangzhou Medical College, Guangzhou, China (1) The effects of Immunsyn E on eleven cancer cases were investigated by Guangzhou Institute of Respiratory Diseases. After examining 8 cases of cancer patients who had their records better kept than the other 3 cases, 6 out of the 8 were proven effective in which three case are complete remission and three cases show partial remission with the following characteristics: (i) tumor sizes reduced; (ii) severe pain caused by cancer relieved; and (iii) tumor regression occurred in relatively short treatment period (i.e., a malignant tongue cancer shrank significantly after the shortest injecting period of 10 days). Among these different kinds of cancer, treatment results disclosed that breast cancer and tongue sarcoma were most effected, melanoma, lymphatic tumor and waist sarcoma showed evidence of some improvement, while the results for liver cancer were unsure.

(2) The relationship between the amount of dosages, means of intake, and method of application.

Most of the patients started with small dosages of I.M. or I.T. (muscle injection or tumoral local injection), and began with 1.5 ml/day, gradually increasing to 3–5 ml/day. The maximum dosage used per day was I.T.+I.M.=6 ml. All dosages used were proven safe to the patient. In some occasion oral gels were added but not counted for.

The best result came from tumoral injection. i.e., directly injecting Immunsyn E into the tumor. In the alternative, there were 2 alternative ways for injection. The first method is to start injection Inmunsyn E right on the center portion of the tumor and then move the needle points to the outer rim of the tumor. The second method is to inject Immunsyn E all around the tumor, but not touching the tumor. The second method of injection comparatively was more effective. Regardless of which method of tumoral injection was used, it was important to make sure the injections have to reach the bottom part of the tumor and the multiple injections uniformly distributed. Otherwise, the cancer cells may be still alive at the deep bottom of the tumor.

(3) Side effects and patient reactions

During the time of administering the Immunsyn E, a majority of patients felt drowsy and occasionally dizzy. It is advisable to start with a smaller dosage, and to slow down the speed of administration. There were no other side effects observed. In the meantime, Immunsyn E has shown astonishing pain-killing abilities because most of the patients showed relief from severe pains which are otherwise caused by the tumor in the absence of Immunsyn E injection.

(4) Experimental data and the human life vital signs:

From examining patients blood specimen, the general, Hgb(g/b), WBC & GLT kept normal or dropped slightly. Liver and kidney functions showed no changes at all, the immune ability and bone marrow showed no suppression. All the patients showed encouragingly well vital signs and patients' conditions kept improving throughout the entire treatments.

In conclusion, Immunsyn E may be considered as a good anti-cancer drug to treat those patients with late stage terminal cancer, and/or those not operable. Its activity in treating cancer effectively was verified through the human clinical investigation. In addition, its side-effects were small when compared with the conventional chemotherapy.

F. Barrow's Tumor Institute Summary Report

Barrows Tumor Institute of Guangzhou is an independently operated cancer hospital which was established to treat only cancer patients. The department of health of Guangzhou city granted a special permit which made Immunsyn E to treat terminally ill cancer patients possible.

(1) Tumoral injection and muscle injection of Inmunsyn E.

Of the over 200 stage III and stage IV cancer patients (including a wide range of carcinoma and sarcoma) treated with Immunsyn E in this hospital, there were 43% Complete Remission and Partial Remission (CR+PR), 26% Mimor Remission (MR+SD) and 31% (PD+Death). In consideration of that the above studies were only stage I human investigations, and the patients were all terminally ill cancer patients, the results were considered very promising.

(2) Oral gels and tonics

More than 400 patients have taken oral gels or tonics, 3 to 4 pieces (4 PCs.=345 mg of Immunsyn E) daily, each gel contains 0.25 ml of Immunsyn E; basically gels work as a maintenance drug which seems to delay the recurrences.

(3) Intravenous injections (I.V.) of Immunsyn E.

In general, I.V. is more effective than IM; for those patients with cancer related severe pains (such as liver pain and bone pain) Immunsyn E can also act as an excellent pain killer, some time it worked even better than morphine.

(4) Side effects

There were no side-effects as hair loss, bone marrow suppression, immune suppression. Some patients felt sleepy, loss of appetite, but symptoms subsided when treatment stopped.

What is claimed is:

1. A pharmaceutical composition exhibiting both in vitro and in vivo anti-cancer and tumor necrotizing activity, comprising;
    (a) at least one toluene sulfonamide in an amount of 10–80 percent by weight of said composition;
    (b) a solution prepared from a group consisting of polyethylene glycol, 2-ethyl-1.3-hexanediol, propanediol, decanedioic acid, dimethyl sulfoxide, and ethanol wherein said solution is in an amount of 90–20 percent by weight of said composition ; and
    (c) said toluene sulfonamide is added to said solution on a percentage weight basis to form a mixture sufficient to exhibit said in vitro and in vivo anti-cancer and tumor necrotizing activity.

2. The pharmaceutical composition of claim 1 wherein said toluene sulfonamide is in an amount of 30% by weight of said composition.

3. The pharmaceutical composition of claim 1 wherein said toluene sulfonamide comprises a group of toluene sulfonamide analogs consisting of para-toluene sulfonamide, orthotoluene sulfonamide, N-ethyl orthotoluene, N-ethyl para-toluene sulfonamide, N-cyclohexyl para-toluene sulfonamide or mixtures thereof.

4. The pharmaceutical composition of claim 1 wherein said polyethylene glycol is in an amount of 10%–60% by weight of said composition.

5. The pharmaceutical composition of claim 4 wherein said polyethylene glycol is in an amount of 35.5% by weight of said composition.

6. The pharmaceutical composition of claim 1 wherein said 2-ethyl-1, 3-hexanediol is in an amount of 5%–30% by weight of said composition.

7. The pharmaceutical composition of claim 6 wherein said 2-ethyl-1, 3-hexanediol is in an amount of 16.4% by weight of said composition.

8. The pharmaceutical composition of claim 1 wherein said propanediol is in an amount of 2%–30% by weight of said composition.

9. The pharmaceutical composition of claim 8 wherein said propanediol is in an amount of 8.2% by weight of said composition.

10. The pharmaceutical composition of claim 1 wherein said decanedioic acid is in an amount of 1%–15% by weight of said composition.

11. The pharmaceutical composition of claim 10 wherein said decanedioic acid is in an amount of 3.7% by weight of said composition.

12. The pharmaceutical composition of claim 1 wherein said dimethyl sulphoxide is in an amount of 0%–12% by weight of said composition.

13. The pharmaceutical composition of claim 12 wherein said dimethyl sulphoxide is in an amount of 6.7% by weight of said composition.

14. The pharmaceutical composition of claim 1 wherein said ethanol is in an amount of 0%–12% by weight of said composition.

15. The pharmaceutical composition of claim 14 wherein said ethanol is in an amount of 1.5% by weight of said composition.

16. A pharmaceutical composition exhibiting anti-cancer and tumor necrotizing activity in a human recipient to provide therapeutical benefits by injection, comprising;
    (a) at least one toluene sulfonamide in an amount of 10–80 percent by weight of said composition;
    (b) a solution prepared from a group consisting of polyethylene glycol, 2-ethyl-1.3-hexanediol, propanediol, decanedioic acid, dimethyl sulfoxide, and ethanol wherein said solution is in an amount of 90–20 percent by weight of said composition ; and
    (c) said toluene sulfonamide is added to said solution on a percentage weight basis to form a mixture sufficient to exhibit said anti-cancer and tumor necrotizing activity in said human recipient.

17. The pharmaceutical composition of claim 16 wherein said toluene sulfonamide is in an amount of 30% by weight of said composition.

18. The pharmaceutical composition of claim 16 wherein said toluene sulfonamide comprises a group of toluene sulfonamide analogs consisting of para-toluene sulfonamide, orthotoluene sulfonamide, N-ethyl orthotoluene, N-ethyl para-toluene sulfonamide, N-cyclohexyl para-toluene sulfonamide or mixtures thereof.

19. The pharmaceutical composition of claim 16 wherein said polyethylene glycol is in an amount of 10%–60% by weight of said composition.

20. The pharmaceutical composition of claim 19 wherein said polyethylene glycol is in an amount of 35.5% by weight of said composition.

21. The pharmaceutical composition of claim 16 wherein said 2-ethyl-1, 3-hexanediol is in an amount of 5%–30% by weight of said composition.

22. The pharmaceutical composition of claim 21 wherein said 2-ethyl-1, 3-hexanediol is in an amount of 16.4% by weight of said composition.

23. The pharmaceutical composition of claim 16 wherein said propanediol is in an amount of 2%–30% by weight of said composition.

24. The pharmaceutical composition of claim 23 wherein said propanediol is in an amount of 8.2% by weight of said composition.

25. The pharmaceutical composition of claim 16 wherein said decanedioic acid is in an amount of 1%–15% by weight of said composition.

26. The pharmaceutical composition of claim 25 wherein said decanedioic acid is in an amount of 3.7% by weight of said composition.

27. The pharmaceutical composition of claim 16 wherein said dimethyl sulphoxide is in an amount of 0%–12% by weight of said composition.

28. The pharmaceutical composition of claim 27 wherein said dimethyl sulphoxide is in an amount of 6.7% by weight of said composition.

29. The pharmaceutical composition of claim 16 wherein said ethanol is in an amount of 0%–12% by weight of said composition.

30. The pharmaceutical composition of claim 29 wherein said ethanol is in an amount of 1.5% by weight of said composition.

31. A method of preparing a pharmaceutical composition exhibiting both in vitro and in vivo anti-cancer and tumor necrotizing activity, comprising;
    (a) weighing at least one toluene sulfonamide in an amount of 10–80 percent by weight of said composition;

(b) preparing a solution from a group consisting of polyethylene glycol, 2-ethyl-1.3-hexanediol, propanediol, decanedioic acid, dimethyl sulfoxide, and ethanol wherein said solution is in an amount of 90–20 percent by weight of said composition; and (c) adding said toluene sulfonamide to said solution on a percentage weight basis to form a mixture sufficient to exhibit said in vitro and in vivo anti-cancer and tumor necrotizing activity.

32. The method of claim 31 wherein said toluene sulfonamide is in an amount of 30% by weight of said composition.

33. The method of claim 31 wherein said toluene sulfonamide comprises a group of toluene sulfonamide analogs consisting of para-toluene sulfonamide, orthotoluene sulfonarnide, N-ethyl orthotoluene, N-ethyl para-toluene sulfonamide, N-cyclohexyl para-toluene sulfonamide or mixtures thereof.

34. The method of claim claim 31 wherein said solution is in an amount of 70% by weight of said composition.

35. A method of preparing a pharmaceutical composition exhibiting anti-cancer and tumor necrotizing activity in a human recipient to provide therapeutical benefits, comprising;

(a) weighing at least one toluene sulfonamide in an amount of 10–80 percent by weight of said composition;

(b) preparing a solution from a group consisting of polyethylene glycol, 2-ethyl-1.3-hexanediol, propanediol, decanedioic acid, dimethyl sulfoxide, and ethanol wherein said solution is in an amount of 90–20 percent by weight of said composition; and (c) adding said toluene sulfonamide to said solution on a percentage weight basis to form a mixture sufficient to exhibit said anti-cancer and tumor necrotizing activity in said human recipient.

36. The method of claim 35 wherein said toluene sulfonamide is in an amount of 30% by weight of said composition.

37. The method of claim 35 wherein said toluene sulfonamide comprises a group of toluene sulfonamide analogs consisting of para-toluene sulfonamide, orthotoluene sulfonamnide, N-ethyl orthotoluene, N-ethyl para-toluene sulfonamide, N-cyclohexyl para-toluene sulfonamide or mixtures thereof.

38. The method of claim 35 wherein said solution is in an amount of 70% by weight of said composition.

39. A method of providing therapeutical benefits to a human patient diagnosed with a cancer lesion, comprising:

(a) preparing a pharmaceutical composition exhibiting anti-cancer and tumor necrotizing activity, said pharmaceutical composition comprising (i) at least one toluene sulfonamide in an amount of 10–80 percent by weight of said composition; (ii) a solution prepared from a group consisting of polyethylene glycol, 2-ethyl-1.3-hexanediol, propanediol, decanedioic acid, dimethyl sulfoxide, and ethanol wherein said solution is in an amount of 90–20 percent by weight of said composition; and (iii) adding said toluene sulfonamide to said solution on a percentage weight basis to form a mixture sufficient to exhibit said anti-cancer and tumor necrotizing activity; and (b) injecting said human patient repeatedly with an amount of said pharmaceutical composition sufficient to exhibit said anti-cancer and tumor necrotizing activity in said human patient.

40. A method of claim 39 wherein said pharmaceutical composition is being injected to said human patient directly to said cancer lesion.

41. A method of necrotizing cancer cells or a tumor in a human patient to provide therapeutical benefits, comprising;

(a) preparing a pharmaceutical composition exhibiting anti-cancer and tumor necrotizing activity, said pharmaceutical composition comprising (i) at least one toluene sulfonamide in an amount of 10–80 percent by weight of said composition; (ii) a solution prepared from a group consisting of polyethylene glycol, 2-ethyl-1.3-hexanediol, propanediol, decanedioic acid, dimethyl sulfoxide, and ethanol wherein said solution is in an amount of 90–20 percent by weight of said composition; and (iii) adding said toluene sulfonamide to said solution on a percentage weight basis to form a mixture sufficient to exhibit said anti-cancer and tumor necrotizing activity; and (b) injecting said cancer cells or tumors repeatedly each with an adequate interval with an amount of said pharmaceutical composition sufficient to exhibit said anti-cancer or tumor necrotizing activity in said human patient.

* * * * *